(12) United States Patent
Sakata et al.

(10) Patent No.: US 11,844,642 B2
(45) Date of Patent: Dec. 19, 2023

(54) TREATMENT SYSTEM, CALIBRATION METHOD, AND STORAGE MEDIUM

(71) Applicant: Toshiba Energy Systems & Solutions Corporation, Kawasaki (JP)

(72) Inventors: Yukinobu Sakata, Kawasaki (JP); Ryusuke Hirai, Shinagawa (JP); Akiyuki Tanizawa, Kawasaki (JP); Shinichiro Mori, Chiba (JP); Keiko Okaya, Setagaya (JP)

(73) Assignee: Toshiba Energy Systems & Solutions Corporation, Kawasaki (JP)

( * ) Notice: Subject to any disclaimer, the term of this patent is extended or adjusted under 35 U.S.C. 154(b) by 528 days.

(21) Appl. No.: 17/152,989

(22) Filed: Jan. 20, 2021

(65) Prior Publication Data

US 2021/0137485 A1 May 13, 2021

Related U.S. Application Data

(63) Continuation of application No. PCT/JP2019/029176, filed on Jul. 25, 2019.

(30) Foreign Application Priority Data

Jul. 26, 2018 (JP) .................................. 2018-140736

(51) Int. Cl.
 *A61B 6/00* (2006.01)
 *G06T 7/80* (2017.01)
 (Continued)

(52) U.S. Cl.
 CPC ............ *A61B 6/585* (2013.01); *A61N 5/1049* (2013.01); *G06T 7/70* (2017.01); *G06T 7/80* (2017.01);
 (Continued)

(58) Field of Classification Search
 CPC .. A61N 5/1049; A61N 5/1075; A61N 5/1069; A61N 5/1081; A61N 5/1065;
 (Continued)

(56) References Cited

U.S. PATENT DOCUMENTS 6,307,914 B1 10/2001 Kunieda et al.
10,297,042 B2 * 5/2019 Berlinger ............. A61B 6/5229
(Continued)

FOREIGN PATENT DOCUMENTS

JP 2000-167072 A 6/2000
JP 2003-117009 A 4/2003
(Continued)

*Primary Examiner* — Irakli Kiknadze
(74) *Attorney, Agent, or Firm* — Oblon, McClelland, Maier & Neustadt, L.L.P.

(57) ABSTRACT

A treatment system of embodiments includes an imaging system including one or more radiation sources and a plurality of detectors, a first acquirer, a second acquirer, a first deriver, a second deriver, and a calibrator. The radiation sources radiate radiation to an object in a plurality of different directions. The plurality of detectors detect the radiation at different positions. The first acquirer acquires images based on the radiation. The second acquirer acquires position information of a first imaging device in a three-dimensional space. The first deriver derives the position of the object in the images. The second deriver derives the position of a second imaging device in the three-dimensional space based on the position of the object in the images, the position of the first imaging device, and the like. The calibrator performs calibration of the imaging system based on a derivation result of the second deriver.

13 Claims, 10 Drawing Sheets

(51) Int. Cl.
*G06T 7/70* (2017.01)
*A61N 5/10* (2006.01)
*A61B 6/03* (2006.01)

(52) U.S. Cl.
CPC ....... *A61B 6/032* (2013.01); *A61N 2005/1061* (2013.01); *G06T 2207/10081* (2013.01); *G06T 2207/30244* (2013.01)

(58) Field of Classification Search
CPC .... A61N 2005/1076; A61N 2005/1061; A61N 5/1077; A61N 5/1031; A61N 5/1039; A61N 5/1067; A61N 5/103; A61N 2005/105; A61N 2005/1062; A61N 5/1064; A61N 5/107; A61N 2005/1059; A61N 5/1044; A61B 6/4007; A61B 6/5211; A61B 6/4266; A61B 6/585; A61B 6/583; A61B 6/4014; A61B 6/547; A61B 6/032; A61B 6/5241; A61B 6/00; A61B 2034/2065; A61B 2090/364; A61B 2034/2055; G06T 7/80; G06T 7/70; G06T 7/73; G06T 2207/30244; G06T 2207/10116; G06T 2207/30204; G06T 2207/10081; G06T 11/003; G06T 7/344; G06T 2207/30096; G06T 7/32; G06T 7/75; G06T 7/0012; G06T 2207/30004; G06T 2207/10104; G06T 2207/20221; G06T 2207/10028; G06T 2207/10088; G06T 2207/10108; G06T 11/008; G06T 15/08; G06T 7/30; G06T 2207/10072; G06T 2207/10124; G06V 10/143; G06V 10/761; G06V 10/754; G06V 2201/033; G06V 10/62; G06F 18/22
USPC .............................................. 378/4, 19, 207
See application file for complete search history.

(56) References Cited

U.S. PATENT DOCUMENTS

| | | | | |
|---|---|---|---|---|
| 2015/0036793 | A1* | 2/2015 | Umekawa | A61B 6/541 |
| | | | | 378/8 |
| 2015/0117605 | A1* | 4/2015 | Sugiura | G06T 7/73 |
| | | | | 378/62 |
| 2016/0148401 | A1* | 5/2016 | Hirai | A61N 5/107 |
| | | | | 600/1 |
| 2017/0046856 | A1 | 2/2017 | Hirai et al. | |
| 2021/0038917 | A1* | 2/2021 | Karasawa | G06F 3/147 |

FOREIGN PATENT DOCUMENTS

| | | |
|---|---|---|
| JP | 2016-221156 A | 12/2016 |
| JP | 2017-35314 A | 2/2017 |

* cited by examiner

| PATIENT (TEST OBJECT) | TREATMENT DATE AND TIME | BEAM RADIATION ANGLE $\theta$ [°] | ... |
|---|---|---|---|
| A | JUNE 1 2020 | 90 | ... |
| B | JUNE 1 2020 | 45 | ... |
| C | JUNE 1 2020 | 30 | ... |
| D | JUNE 2 2020 | 60 | ... |
| E | JUNE 2 2020 | 70 | ... |
| F | JUNE 2 2020 | 30 | ... |
| ... | ... | ... | ... |

TREATMENT SYSTEM, CALIBRATION METHOD, AND STORAGE MEDIUM

CROSS-REFERENCE TO RELATED APPLICATIONS

This application is based upon and claims the benefit of priority from Japanese Patent Application No. 2018-140736, filed Jul. 26, 2018 and International Application No. PCT/JP2019/029176, filed Jul. 25, 2019; the entire contents all of which are incorporated herein by reference.

FIELD

Embodiments described herein relate generally to a treatment system, a calibration method, and a storage medium.

BACKGROUND

In treatment using radiation, it is necessary to perform calibration of an imaging system such as a flat panel detector (FPD) and an X-ray tube before treatment in order to realize high-accuracy positioning and tumor tracking for a patient. With respect to this, a technology in which a phantom with a marker having a known position in a three-dimensional space of a treatment room is installed at a predetermined position in the treatment room, the installed phantom is imaged with radiation, the position of the marker is derived from the captured image, and an imaging system is calibrated based on the marker position derived from the image and the known marker position in the three-dimensional space is known.

However, in the conventional technology, there are cases in which calibration with high accuracy cannot be performed when the three-dimensional position of the marker is not known or the known three-dimensional position of the marker includes an error. Consequently, there are cases in which the position of a test object such as a patient cannot be determined with high accuracy or a target such as a tumor cannot be tracked with high accuracy.

DETAILED DESCRIPTION

According to one embodiment, a treatment system includes an imaging system including one or more radiation sources and a plurality of detectors as imaging devices, a first acquirer, a second acquirer, a first deriver, a second deriver, and a calibrator. The radiation sources radiate radiation to a certain object in a plurality of different directions. The plurality of detectors detect the radiation radiated from the radiation sources at different positions. The first acquirer acquires a plurality of images based on the radiation detected by the plurality of detectors. The second acquirer acquires position information representing at least one of the position and the direction of a first imaging device included in the imaging system in a three-dimensional space in which the imaging system is disposed. The first deriver derives the position of the object in each of the plurality of images acquired by the first acquirer. The second deriver derives at least one of the position and the direction of a second imaging device included in the imaging system in the three-dimensional space based on the position of the object in the images derived by the first deriver and the position or the direction of the first imaging device represented by the position information acquired by the second acquirer. The calibrator performs calibration of the imaging system based on a derivation result of the second deriver.

According to the present embodiment, it is possible to provide a treatment system, a calibration method, and a storage medium capable of determining the position of a test object with high accuracy and tracking a target with high accuracy.

Hereinafter, a treatment system, a calibration method, and a storage medium of embodiments will be described with reference to the drawings.

First Embodiment

Figure 1:
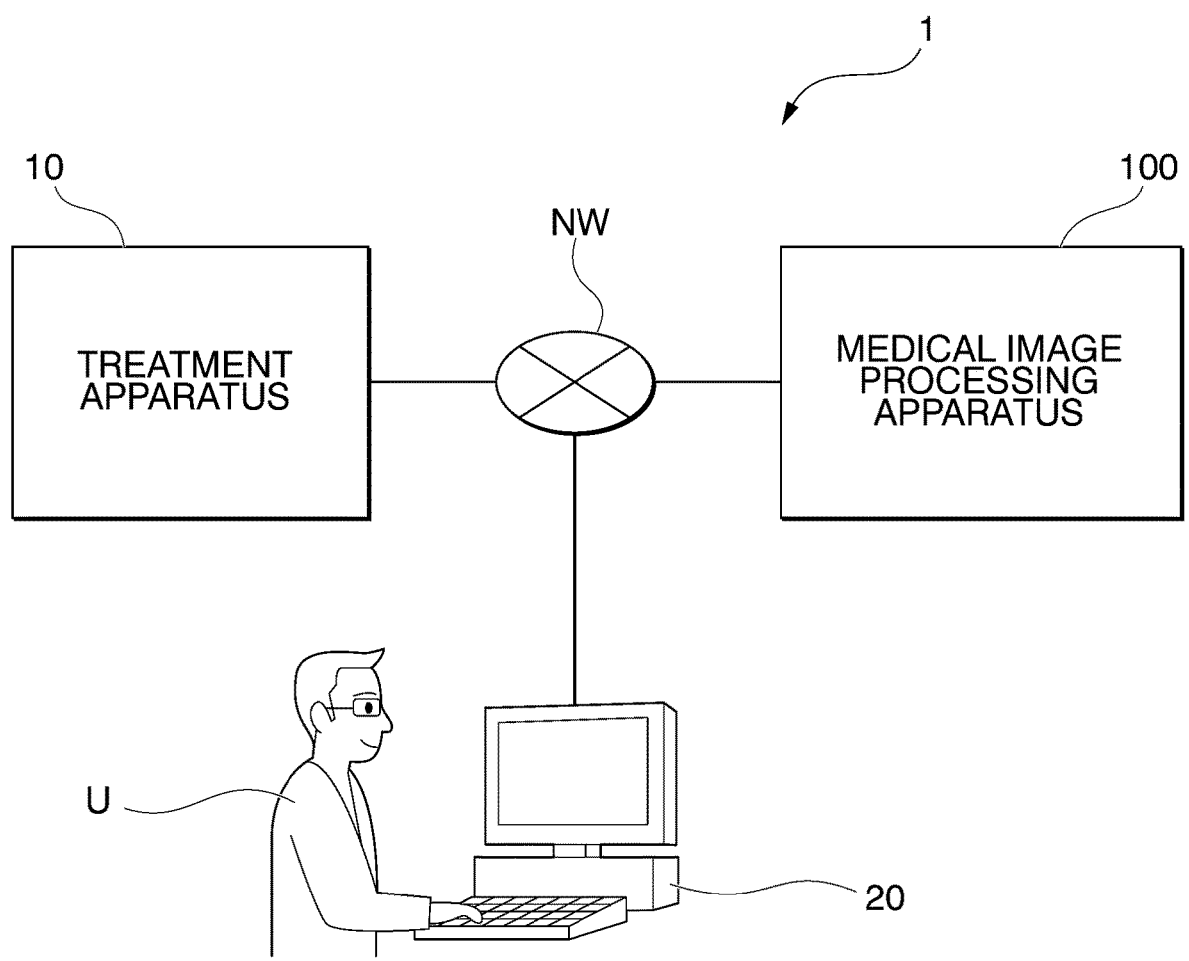
FIG. 1 is a diagram showing an example of a treatment system in a first embodiment.

FIG. 1 is a diagram showing an example of a treatment system 1 in a first embodiment. For example, the treatment system 1 includes a treatment apparatus 10, a terminal apparatus 20, and a medical image processing apparatus 100. These apparatuses are connected through a network NW. The network NW includes, for example, the Internet, a wide area network (WAN), a local area network (LAN), a provider terminal, a wireless communication network, a wireless base station, a dedicated line, and the like. All combinations of the apparatuses shown in FIG. 1 need not communicate with each other and a part of the network NW may include a local network.

The treatment apparatus 10 is an apparatus which radiates first radiation as a beam (hereinafter referred to as a treatment beam B) to a test object OB in any direction of 360° with the test object OB as a center. The test object OB is a patient who receives treatment using the treatment beam B, for example. The first radiation includes, for example, particle radiation such as a heavy particle beam, an electron beam, a proton beam, and a neutron beam, and electromagnetic radiation such as X-rays and y-rays. The treatment apparatus 10 radiates second radiation to generate a tomographic image of the test object OB in order to check the position of the test object OB. The second radiation includes, for example, electromagnetic radiation such as X-rays. Hereinafter, an example in which the first radiation (treatment beam B) is a "heavy particle beam" and the second radiation is "X-rays" will be described.

The terminal apparatus 20 is used by a user (hereinafter referred to as a maintenance operator U) who performs maintenance such as preparation and maintenance, repairing, inspection and trimming of the treatment apparatus 10. For example, the terminal apparatus 20 may be a terminal apparatus including an input device, a display device, a communication device, a storage device, and an arithmetic device, such as a cellular phone such as a smartphone, a tablet terminal, and various personal computers. The communication device of the terminal apparatus 20 includes a network card such as a network interface card (NIC), a wireless communication module, and the like.

The medical image processing apparatus 100 tracks a target moving according to the respiration and movement of the heartbeat of a patient that is a test object OB and radiates the treatment beam B to the treatment apparatus 10 with respect to the tracked target at an appropriate timing. The target is an organ such as a lung or the liver. Tracking of this target is performed based on a tomographic image of the test object OB captured using X-rays or the like in a stage prior to a treatment stage and a transparent image obtained by imaging the test object OB in the treatment stage.

The medical image processing apparatus 100 may derive a position gap between the position of the test object OB in the treatment stage and the position of the test object OB when a treatment plan has been formed and provide information about the derived position gap to a person (a doctor or the like) who performs radiation treatment using the treatment system 1.

Figure 2:
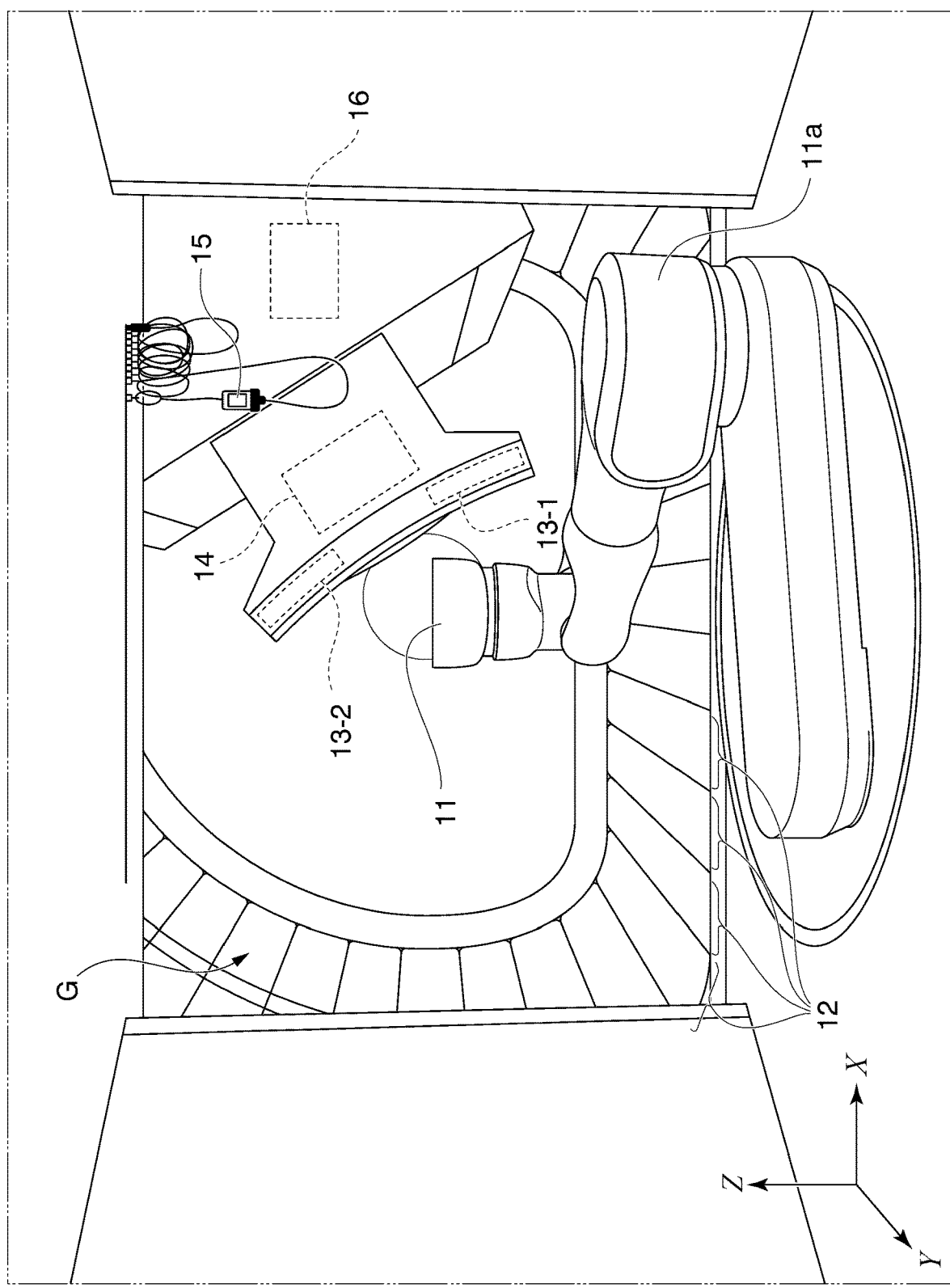
FIG. 2 is an external view of a treatment apparatus in the first embodiment.

FIG. 2 is an external view of the treatment apparatus 10 in the first embodiment. The treatment apparatus 10 in the first embodiment includes, for example, a bed 11, an arm 11a, a plurality of radiation sources (radiation radiating holes) 12, two detectors 13-1 and 13-2, a radiating gate 14, a sensor 15, and a treatment apparatus controller 16. The two detectors 13-1 and 13-2 are an example of "detectors."

The plurality of radiation sources 12, the two detectors 13-1 and 13-2, and the radiating gate 14 are provided in a housing in a ring shape (torus shape) which is called a rotary gantry G. For example, when the vertical direction of a three-dimensional space representing a room (hereinafter referred to as a treatment room) in which the treatment apparatus 10 is installed is denoted by $Z_f$, one side of the horizontal direction is denoted by $X_f$ and the other side is denoted by $Y_f$, the rotary gantry G is installed with the direction $Y_f$ as a rotation axis such that it can rotate 360° on the rotation axis. The rotary gantry G is an example of an "imaging system" and each of the plurality of radiation sources 12 and the two detectors 13-1 and 13-2 provided in the rotary gantry G is an example of an "imaging device." The radiating gate 14 is an example of a "particle beam source."

The test object OB is fixed to the bed 11. The arm 11a has one end fixed to the floor or the like of the treatment room and the other end fixed to the bed 11 and moves the bed 11 from the outside to the inside or from the inside to the outside of the rotary gantry G in a state in which the bed 11 is separated from the floor or the like of the treatment room.

The plurality of radiation sources 12 are arranged at predetermined intervals in a circumferential direction of the rotary gantry G, for example. Each radiation source 12 radiates, for example, X-rays to the inner circumferential side of the rotary gantry G. Accordingly, when the bed 11 moves to the inside of the rotary gantry G, for example, X-rays are radiated to the test object OB fixed to the bed 11 in a plurality of different directions of 360°. A radiation generation device (not shown) that generates X-rays may be installed outside the treatment room.

The detectors 13-1 and 13-2 detect, for example, X-rays radiated from the radiation sources 12. For example, the detectors 13-1 and 13-2 include a rectangular detector such as a flat panel detector (FPD), an image intensifier or a color image intensifier. For example, the detectors 13-1 and 13-2 convert an analog signal based on detected X-rays into a digital signal and output the digital signal to the medical image processing apparatus 100 as a transparent image TI. The transparent image TI is a two-dimensional image and is a tomographic image of the test object OB. The number of detectors provided in the rotary gantry G is not limited to 2 and may be 3 or more.

The radiating gate 14 is provided at a certain position in the circumferential direction of the rotary gantry G. The radiating gate 14 radiates the treatment beam B to the inner circumferential side of the rotary gantry G. Although a single radiating gate 14 is provided in the rotary gantry G in the example of FIG. 1, the present invention is not limited thereto. For example, a plurality of radiating gates may be provided in the rotary gantry G. A radiation generation device (not shown) that generates the treatment beam B may be installed outside the treatment room.

The sensor 15 is a sensor which detects movement of an affected part according to respiration of a patient as a phase when the test object OB is the patient. For example, the sensor 15 is a pressure sensor. In this case, the sensor 15 may be attached to the body of the patient. The sensor 15 outputs information representing the detected phase of the respiration of the patient as a waveform to the medical image processing apparatus 100.

The treatment apparatus controller 16 is realized, for example, by a hardware processor such as a central processing unit (CPU) or a graphics processing unit (GPU) executing a program (software) stored in a storage device (not shown) such as a read only memory (ROM). The treatment apparatus controller 16 may be realized by hardware (circuit: circuitry) such as a large scale integration (LSI) circuit, an application specific integrated circuit (ASIC), or a field-programmable gate array (FPGA), or realized by software and hardware in cooperation.

The treatment apparatus controller 16 is controlled by the medical image processing apparatus 100 to operate the plurality of radiation sources 12, the detectors 13-1 and 13-2, and the radiating gate 14. The treatment apparatus controller 16 is controlled by the medical image processing apparatus 100 to rotate the rotary gantry G.

Figure 3:
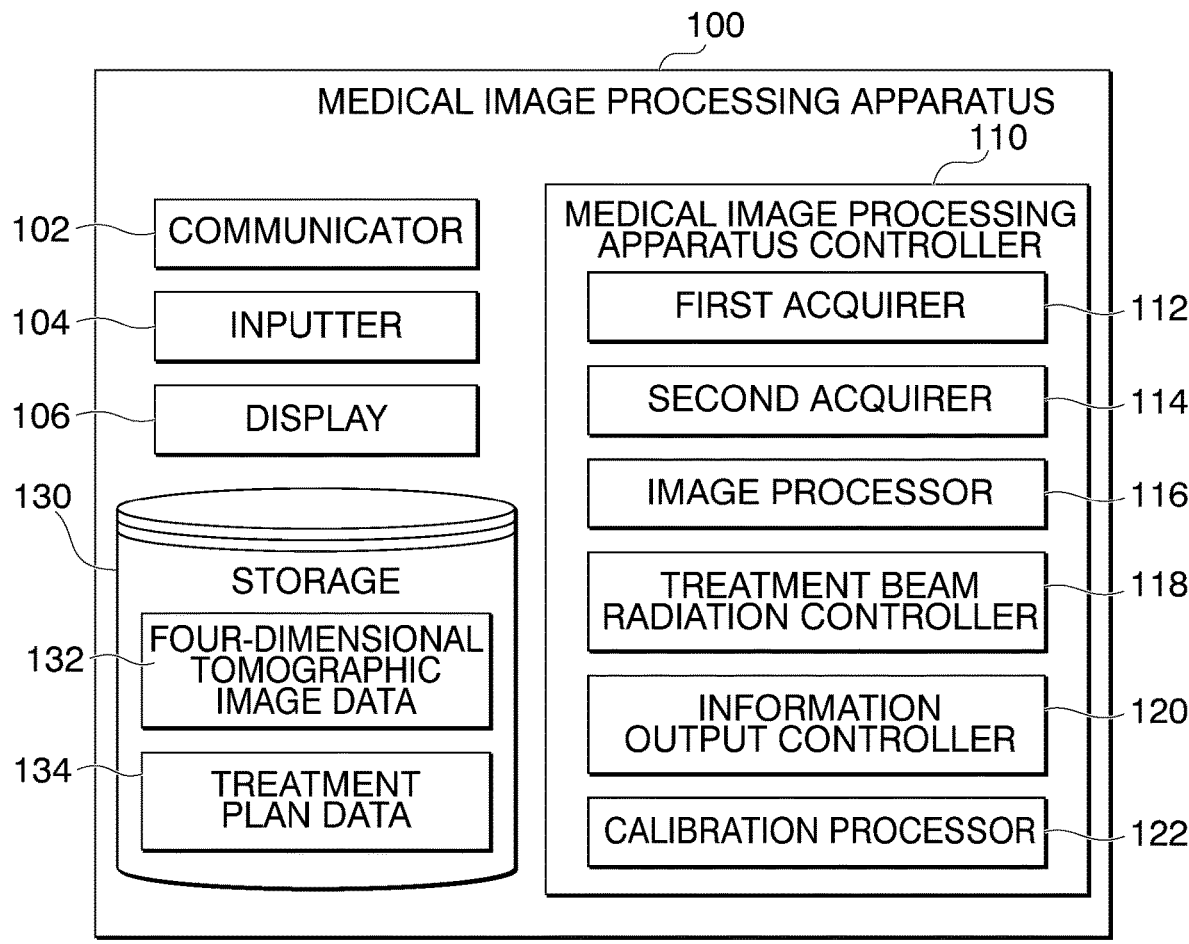
FIG. 3 is a diagram showing an example of a configuration of a medical image processing apparatus in the first embodiment.

FIG. 3 is a diagram showing an example of a configuration of the medical image processing apparatus 100 in the first embodiment. The medical image processing apparatus 100 in the first embodiment includes, for example, a communicator 102, an inputter 104, a display 106, a medical image processing apparatus controller 110, and a storage 130.

The communicator 102 includes, for example, a communication interface such as an NIC. The communicator 102 communicates with the treatment apparatus 10 and the terminal apparatus 20 through the network NW and receives various types of information. The communicator 102 outputs the received information to the medical image processing apparatus controller 110. The communicator 102 may be controlled by the medical image processing apparatus controller 110 to transmit information to the treatment apparatus 10 and the terminal apparatus 20 connected through the network NW. The communicator 102 is an example of an "outputter."

For example, the inputter 104 receives an input operation from a user such as a doctor or a nurse and outputs a signal based on the received input operation to the medical image processing apparatus controller 110. For example, the inputter 104 is realized by a mouse, a keyboard, a trackball, a switch, a button, a joystick, a touch panel, or the like. The inputter 104 may be realized, for example, by a user interface that receives audio input, such as a microphone. When the inputter 104 is a touch panel, the display 106 which will be described later may be integrated with the inputter 104.

The display 106 displays various types of information. For example, the display 106 displays an image generated by the medical image processing apparatus controller 110 or displays a graphical user interface (GUI) or the like for receiving an input operation from an operator. For example, the display 106 is a liquid crystal display (LCD), an organic electroluminescence (EL) display, or the like. The display 106 is another example of the "outputter."

The medical image processing apparatus controller 110 includes, for example, a first acquirer 112, a second acquirer 114, an image processor 116, a treatment beam radiation controller 118, an information output controller 120, and a calibration processor 122. The treatment apparatus controller 16 and the treatment beam radiation controller 118 are an example of a "radiation controller."

These components are realized by a hardware processor such as a CPU or a GPU executing a program (software) stored in the storage 130. Some or all of these components may be realized by hardware (circuit: circuitry) such as an LSI, an ASIC or an FPGA or software and hardware in cooperation. The aforementioned program may be stored in the storage 130 in advance or stored in a detachable storage medium such as a DVD or a CD-ROM and installed into the storage 130 from the storage medium when the storage medium is inserted into a drive device of the medical image processing apparatus 100.

The storage 130 is realized, for example, by a storage device such as a ROM, a flash memory, a random access memory (RAM), a hard disc drive (HDD), a solid state drive (SSD) or a register. The flash memory, HDD, SSD, and the like are non-transient storage media. These non-transient storage media may be realized by other storage devices connected through the network NW, such as a network attached storage (NAS) and an external storage server device. For example, four-dimensional tomographic image data 132, treatment plan data 134, and the like are stored in the storage 130. These will be described later.

For example, the four-dimensional tomographic image data 132 is time-series arrangement of n three-dimensional tomographic images (CT images) that are three-dimensional volume data. The three-dimensional tomographic images are captured in a treatment planning stage, for example. A period obtained by multiplying n by the time interval of the time-series images is set such that it covers a period in which a respiration phase changes by one cycle, for example. The respiration phase is a phase having a period from when a patient exhales and then inhales to when the patient exhales again as one cycle. For example, n=10. For example, an area indicating the outline of a tumor that is an affected part, an area indicating the outline of an organ to which the treatment beam B is not desired to be radiated, and the like are set by an input operation of a doctor or the like in the image area of at least one of the n three-dimensional tomographic images. In other three-dimensional tomographic images, the same areas as the areas of the outlines set by the input operation of the doctor or the like are automatically set according to deformable registration. The deformable registration is processing of expanding position information (the outline of the organ, or the like in the above case) designated with respect to three-dimensional volume data at a certain point in time to three-dimensional volume data at a different point in time for time-series three-dimensional volume data.

The treatment plan data 134 is data representing a treatment plan formed (planned) in the treatment planning stage. The treatment plan is, for example, a plan in which a treatment beam B radiation direction such as a direction in which the treatment beam B will be radiated when a patient that is a test object OB is positioned at a position, and the intensity of the treatment beam B when the treatment beam B is radiated, and the like have been determined for each patient that is a test object OB. This treatment plan may be planned based on a treatment method such as a gated radiation method or a tracking radiation method.

The first acquirer 112 acquires, for example, transparent images TI from the detectors 13-1 and 13-2 through the communicator 102. Since the transparent images TI are generated by the detectors 13-1 and 13-2 in real time during treatment, for example, the first acquirer 112 acquires transparent images TI continuing in time series.

The second acquirer 114 acquires position information representing positions or directions (positions or directions in the three-dimensional space of the treatment room) of one or more of the plurality of imaging devices provided in the rotary gantry G. For example, the three-dimensional positions or directions of the imaging devices are measured by a laser tracker. Here, it is assumed that the position of the laser tracker is determined as a relative position based on an object (e.g., the rotation axis of the rotary gantry G, or the like) that is the origin in the three-dimensional space of the treatment room.

In the present embodiment, as an example, imaging devices having positions or directions measured by the laser tracker will be described as the detectors 13-1 and 13-2. The imaging devices having positions or directions measured by the laser tracker may be the radiation sources 12. For example, when the positions and directions of the detectors 13-1 and 13-2 are measured, a medical professional such as a doctor or a nurse obtains relative positions of a plurality of probes by installing the probes (e.g., reflectors and the like) that easily reflect laser beams at three or more points of the detection planes of the detectors 13-1 and 13-2 and measuring the probes using the laser tracker. Then, the medical professional derives the positions and directions of the detectors 13-1 and 13-2 based on the relative positions of the plurality of probes. An imaging device having the position or direction measured by the laser tracker is an example of a "first imaging device."

When the three-dimensional positions of the imaging devices have been measured by the laser tracker, the second acquirer 114 acquires position information representing the three-dimensional positions of the imaging devices from the laser tracker through the communicator 102. When a doctor or the like inputs position information to the inputter 104, the second acquirer 114 may acquire the information input to the inputter 104 as position information representing the three-dimensional positions of imaging devices. Measurement of the positions or directions of imaging devices is not limited to measurement using the laser tracker and the positions or directions of imaging devices may be measured using a stereo camera or a contact type sensor, for example.

The image processor 116 determines the position of the test object OB. For example, the image processor 116 generates a digitally reconstructed radiograph (DRR) based on a three-dimensional tomographic image of each respiration phase included in four-dimensional tomographic image data 132 of each test object OB stored in the storage 130. A DRR is a virtual transparent image generated from three-dimensional volume data in response to a virtual radiation source when it is assumed that radiation is radiated from the virtual radiation source to the three-dimensional tomographic image (three-dimensional volume data).

For example, the image processor 116 generates a DRR when the three-dimensional tomographic image has been viewed at a viewpoint in the same direction as a radiation direction of X-rays radiated to the current test object OB using a method called 3D-2D registration based on the three-dimensional tomographic image of each respiration phase included in the four-dimensional tomographic image data 132, the transparent image TI on the side of the detector 13-1 and the transparent image TI on the side of the detector 13-2 acquired by the first acquirer 112. When the image processor 116 generates the DRR, the image processor 116 may generate the DRR that is a virtual two-dimensional tomographic image by rendering a three-dimensional tomographic image using a ray casting method. Here, the image processor 116 may integrate each element value of the three-dimensional tomographic image and use the integrated value as an element value of each element of the DRR or use a maximum value of each element value of the three-dimensional tomographic image as an element value of each element of the DRR.

For example, the image processor 116 selects a DRR corresponding to a three-dimensional tomographic image of an exhalation phase from DRRs corresponding to three-dimensional tomographic images of respiration phases as a template image. The exhalation phase is a tomographic image captured in a state in which the patient that is the test object OB has exhaled.

The image processor 116 compares the DRR selected as the template image with transparent images TI sequentially acquired by the first acquirer 112 and performs matching of the position of a target (an organ or the like). When the positions of the target in the DRR and the transparent images TI match, the image processor 116 determines that the respiration phase (exhalation phase) of the three-dimensional image that is the source of the DRR corresponds to the current respiration phase of the patient and permits radiation of the treatment beam B. Here, the image processor 116 may further permit radiation of the treatment beam B when the position of the target is within a radiation area determined in advance. The radiation area may be arbitrarily determined by a medical professional, for example.

The treatment beam radiation controller 118 causes the radiating gate 14 to radiate the treatment beam B to the test object OB at a position determined by the image processor 116 when the image processor 116 permits radiation of the treatment beam B. For example, the treatment beam radiation controller 118 extracts information such as a radiation angle of the treatment beam B and an intensity of the treatment beam B from the treatment plan indicated by the treatment plan data 134 and outputs various types of extracted information to the treatment apparatus controller 16. Upon reception of this, the treatment apparatus controller 16 causes the rotary gantry G to rotate or causes the radiating gate 14 to radiate the treatment beam B.

The information output controller 120 causes the display 106 to display an image or causes the communicator 102 to transmit information, for example, in response to presence or absence of permission to radiate the treatment beam B.

Figure 4:
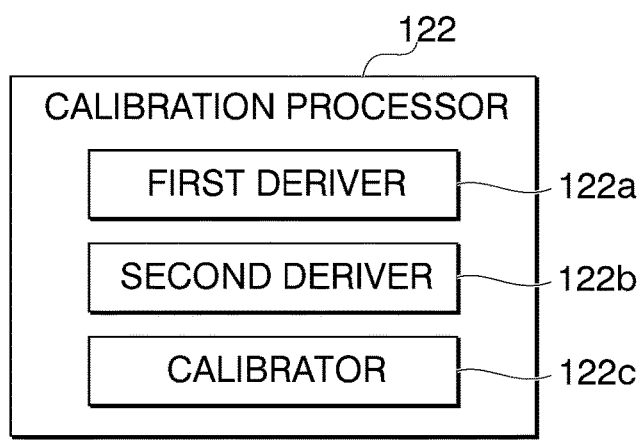
FIG. 4 is a diagram showing an example of a configuration of a calibration processor.

The calibration processor 122 performs calibration of the rotary gantry G. FIG. 4 is a diagram showing an example of a configuration of the calibration processor 122. The calibration processor 122 includes, for example, a first deriver 122a, a second deriver 122b, and a calibrator 122c.

Figure 5:
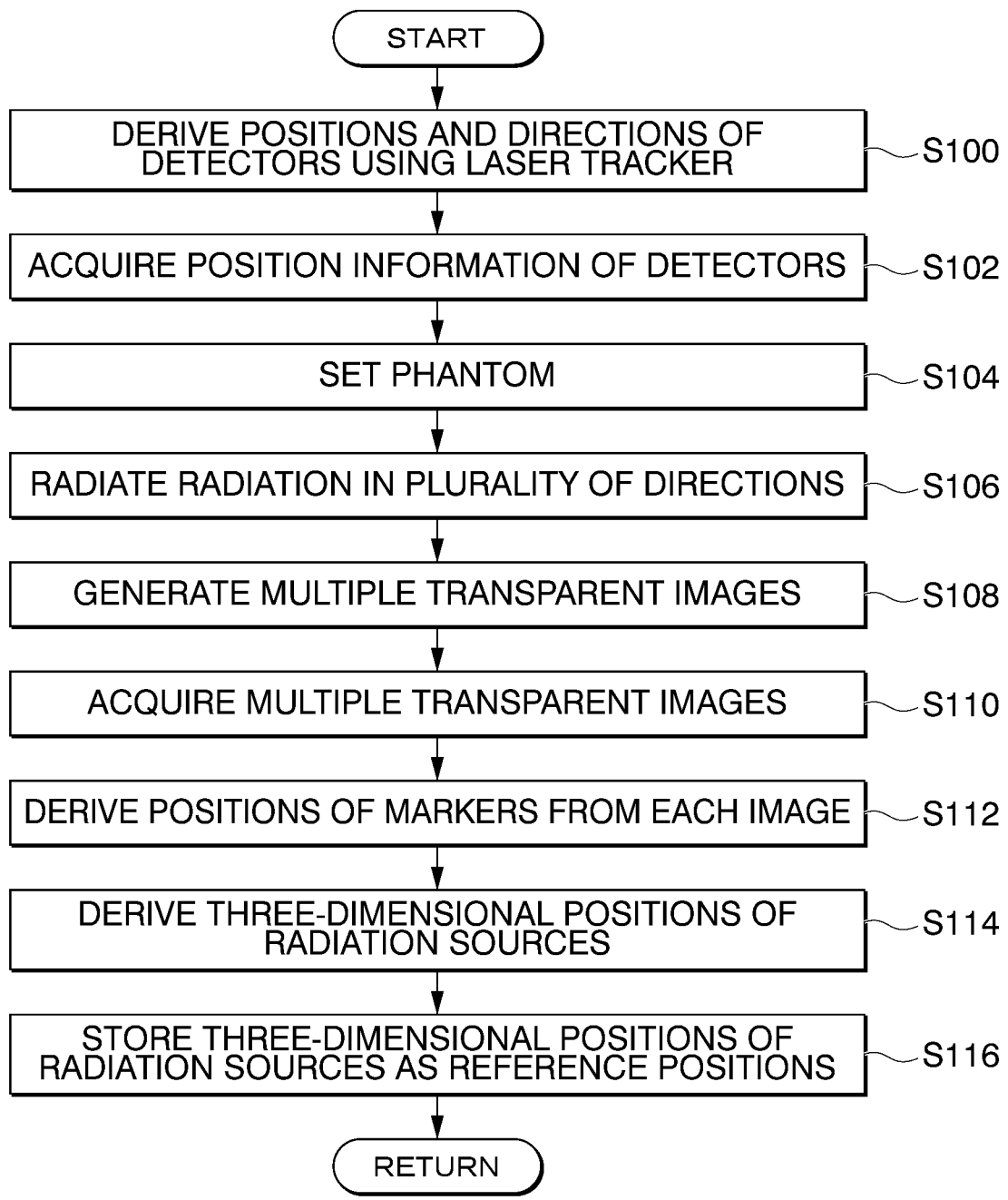
FIG. 5 is a flowchart showing an example of calibration processing.

Hereinafter, processing of each component of the calibration processor 122 will be described using a flowchart. FIG. 5 is a flowchart showing an example of calibration processing. Processing of this flowchart may be repeatedly performed in a first cycle. The first cycle is, for example, a period of approximately one month or several months.

First, a medical professional or the like derives the positions and directions of the detectors 13-1 and 13-2 using a laser tracker or the like (step S100).

Next, the second acquirer 114 acquires position information representing the positions and directions of the detectors 13-1 and 13-2 in the three-dimensional space (step S102). Accordingly, the positions and directions of the detectors 13-1 and 13-2 in the three-dimensional space are handled as known information during calibration.

Next, the medical professional or the like sets a phantom having four or more markers embedded therein inside the rotary gantry G such that the phantom is projected in a transparent image T1 (step S104). The phantom is an acrylic case in a cubic shape, for example.

A marker may be any object that attenuates X-rays, such as an iron ball or a wire, for example. At least one of the four or more markers is embedded in the phantom such that it is present on a plane different from a plane (two-dimensional space) on which the other three or more markers are present in the three-dimensional space in the phantom. Accordingly, a space formed when the markers embedded in the phantom are used as vertices is a three-dimensional space. It is assumed that the positions of these markers and positional relationships between the markers are known in advance.

The medical professional or the like may dispose an object associated with the treatment apparatus 10 such as the bed 11 and the arm 11a inside the rotary gantry G instead of setting the phantom.

Next, the medical professional or the like inputs information about completion of setting of the phantom to the inputter 104. Upon reception of this information, the treatment apparatus controller 16 of the treatment apparatus 10 selects two radiation sources 12 from the plurality of radiation sources 12 and causes the two selected radiation sources 12 to radiate X-rays in a plurality of different directions (step S106).

Figure 6:
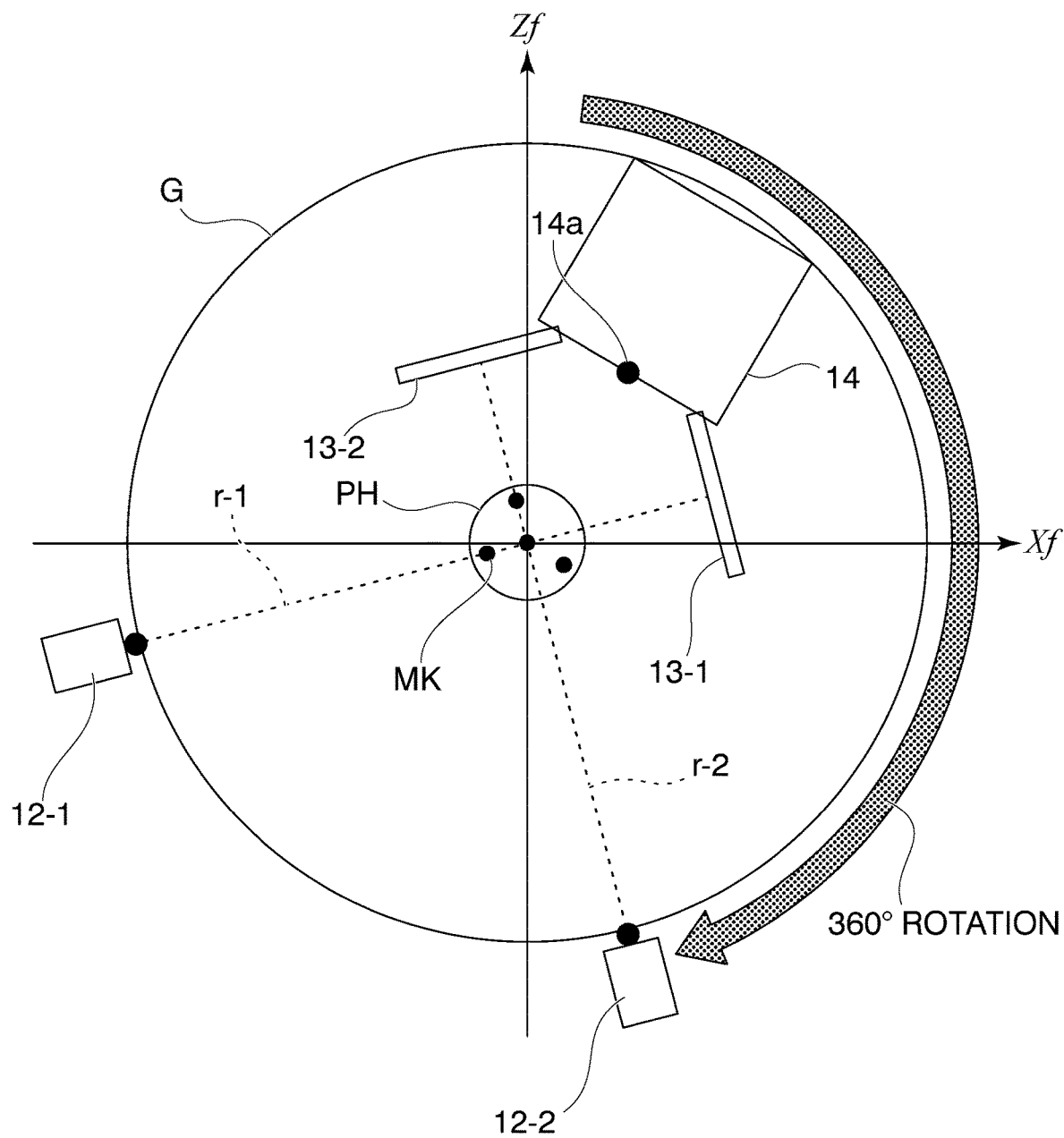
FIG. 6 is a diagram schematically showing a state in which radiation is radiated from two radiation sources.

FIG. 6 is a diagram schematically showing a state in which the two radiation sources 12 are caused to radiate radiation. In the figure, 12-1 represents one radiation source of the two selected radiation sources 12 and 12-2 represents the other radiation source of the two selected radiation sources 12. A broken line r-1 represents X-rays radiated from the radiation source 12-1 and a broken line r-2 represents X-rays radiated from the radiation source 12-2. PH represents a phantom and MK indicates a marker. 14a represents a radiation hole (heavy particle source) of the treatment beam B radiated from the radiating gate 14.

For example, the treatment apparatus controller 16 causes the rotary gantry G to rotate such that an angle around the rotation axis of the rotary gantry G becomes a certain angle θ1 and causes the radiation sources 12-1 and 12-2 to radiate X-rays. Next, the treatment apparatus controller 16 causes the rotary gantry G to rotate such that the angle around the rotation axis of the rotary gantry G becomes an angle θ2 shifted from the angle θ1 by a predetermined angle (e.g., 15°) and causes the radiation sources 12-1 and 12-2 to radiate X-rays. When the rotary gantry G is rotated, the position of the phantom PH (markers MK) imaged using X-rays does not change. In this manner, the treatment apparatus controller 16 causes the detectors 13-1 and 13-2 to generate transparent images TI capturing the phantom PH in a plurality of directions by repeatedly causing the radiation sources 12-1 and 12-2 to radiate X-rays while causing the rotary gantry G to rotate for each predetermined angle width (step S108). For example, when the radiation sources 12-1 and 12-2 radiate X-rays while the angle is changed by 15° in the 360° omni-direction, each of the detectors 13-1 and 13-2 generates 24 transparent images TI (a total of 48 corresponding to the sum of images of the two detectors).

Next, the first acquirer 112 acquires a plurality of transparent images TI from the detectors 13-1 and 13-2 through the communicator 102 (step S110).

Next, the first deriver 122a derives positions of the markers MK with respect to each of the plurality of transparent images TI acquired by the first acquirer 112 (step S112).

For example, the first deriver 122a derives the positions of the markers MK by template-matching a template image prepared in advance and the transparent images T1. An image of the markers MK captured in advance, an image generated through simulation, or the like may be used as the template image. When the shape of the markers MK is known, the first deriver 122a may scan a shape filter for extracting the shape of the markers MK through raster scan or the like for the transparent images T1 and derive positions having high degrees of matching with the shape filter as the positions of the markers MK.

Next, the second deriver 122b derives three-dimensional positions of the radiation sources 12-1 and 12-2 which are unknown parameters based on the positions of the markers MK derived from the transparent images TI and the position information acquired by the second acquirer 114 (step S114). When imaging devices having positions or directions measured by the laser tracker are radiation sources 12, the second deriver 122b may derive the positions and directions of the detectors 13-1 and 13-2 which are unknown parameters. An imaging device having a three-dimensional position derived by the second deriver 122b is an example of a "second imaging device."

For example, when the markers MK are imaged in multiple directions while the rotary gantry G is rotated, three-dimensional positions of the markers MK that are imaging targets are unknown but the positions thereof are invariant. Accordingly, the three-dimensional position of each object can be represented as a common parameter between transparent images TI. For example, the second deriver 122b may derive the positions of the radiation sources 12-1 and 12-2 by applying a method of deriving three-dimensional positions and parameters of an imaging system based on feature points corresponding to each other between multi-view images, such as bundle adjustment. The method called bundle adjustment is a method of adjusting all unknown parameters such that, when markers MK are re-projected onto an image using estimated imaging system parameters, positions of the re-projected markers MK correspond to positions of the markers detected from the image as much as possible.

Figure 7:
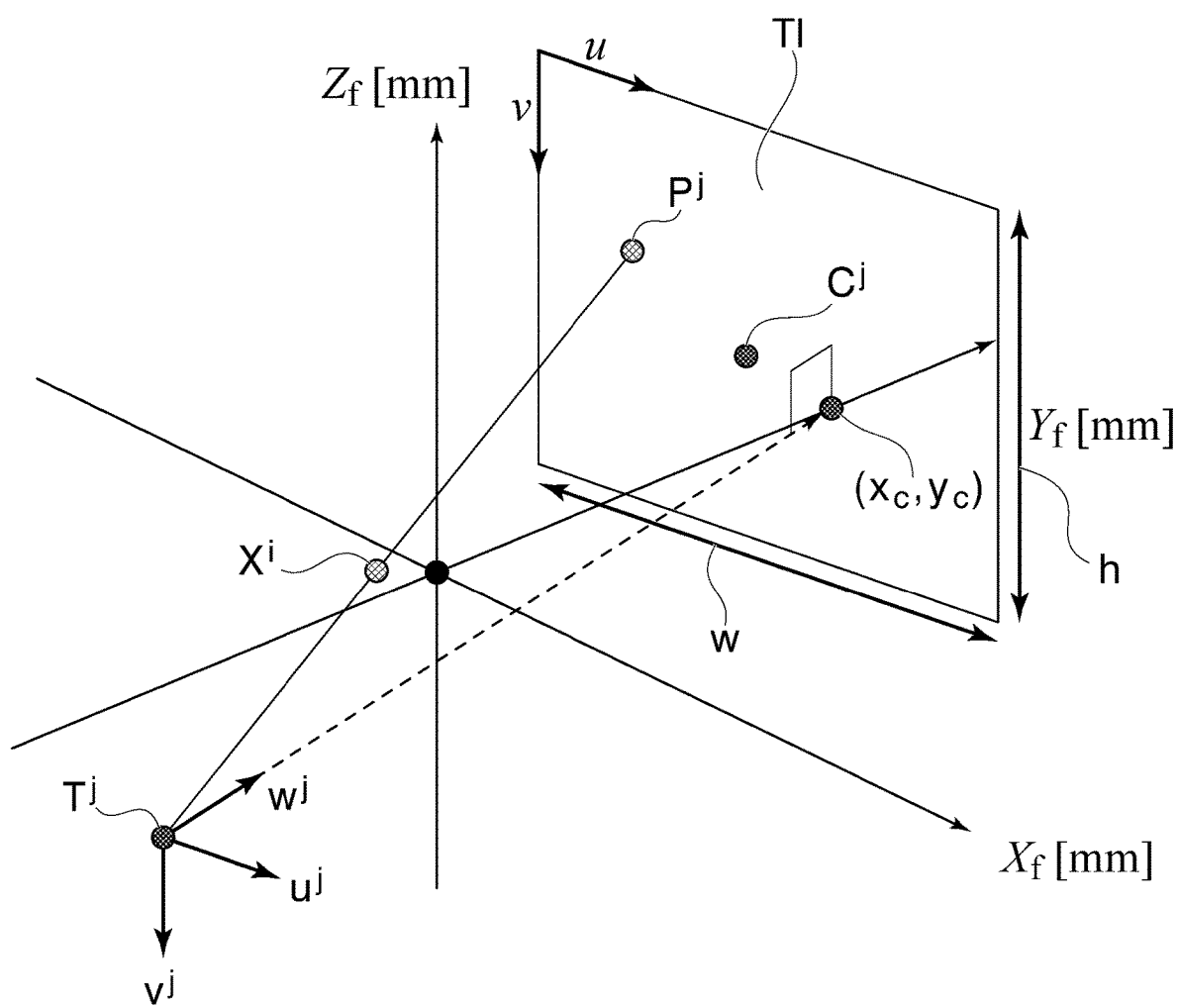
FIG. 7 is a diagram showing a method of deriving a three-dimensional position of a radiation source using a bundle adjustment method.

FIG. 7 is a diagram showing a method of deriving a three-dimensional position of a radiation source 12 according to the bundle adjustment method. For example, when the number of markers MK embedded in the phantom PH is N, a three-dimensional position of each marker MK is represented as $X^i(\rightarrow)=(X^i, Y^i, Z^i)^t$ as in the illustrated example. "i" is any natural number from 1 to N, t represents transposition, and ($\rightarrow$) represents a vector. The position of each marker MK derived from M sets of transparent images TI acquired by imaging at M types of angles is represented as $x^{ij}(\rightarrow)=(x^{ij}, x^{ij})^t$. "j" is any natural number from 1 to M.

When a projection matrix by which the three-dimensional position $X^i(\rightarrow)$ of each marker MK is projected to the plane of a j-th transparent image TI is set to $P^j(\rightarrow)$, the position at which an i-th marker MK should be projected onto the j-th transparent image TI is represented as $x^{ij}(\sim)(\rightarrow)=(x^{ij}(\sim), y^{ij}(\sim))^t$. ($\sim$) represents the tilde symbol. For example, the second deriver 122b derives the position (two-dimensional position in the image) $x^{ij}(\sim)(\rightarrow)$ of the i-th marker MK projected onto the j-th transparent image TI by solving mathematical expression (1).

[Expression 1]

$$\lambda \begin{bmatrix} \tilde{x}^{ij} \\ 1 \end{bmatrix} = P^j \begin{bmatrix} X^i \\ 1 \end{bmatrix} \quad (1)$$

For example, the second deriver 122b searches for various types of parameters that minimize the total (hereinafter referred to as a re-projection error) of sums of squares of differences (variances) between positions $x^{ij}(\sim)(\rightarrow)$ to which the respective markers MK should be projected and derived positions $x^{ij}(\rightarrow)$ of the respective markers MK through bundle adjustment.

For example, the second deriver 122b derives the projection matrix $P^j(\rightarrow)$ based on a base vector $R^j(\rightarrow)=(u^j, v^j, w^j)$ of a detector 13 when the j-th transparent image TI has been captured, a center position $C^j(\rightarrow)=(c_x^i, c_y^i, c_z^i)^t$ of a detection plane of the detector 13 (a center position of the transparent image TI), and a three-dimensional position $T^j(\rightarrow)=(1_x^i, 1_y^i, 1_z^i)^t$ of a radiation source 12. The center position $C^j(\rightarrow)$ of the detection plane of the detector 13 is a three-dimensional position of ((w−1)/2, (h−1)/2) when the width of the transparent image T1 is w and the height is h.

For example, the second deriver 122b derives the projection matrix $P^j(\rightarrow)$ using the above-described parameters based on mathematical expression (2).

[Expression 2]

$$P^j = \begin{bmatrix} \frac{f}{s_u} & 0 & x_c \\ 0 & \frac{f}{s_v} & y_c \\ 0 & 0 & 1 \end{bmatrix} [R^{j^t} - R^{j^t} T^j] \quad (2)$$

In mathematical expression (2), f represents a distance from the three-dimensional position of the radiation source 12 to the three-dimensional position of the detector 13, $s_u$ and $s_v$ represent pixel pitches of axes (u, v) of the transparent image TI, and $x_c$ and $y_c$ represent an intersection position in the image when an optical axis w intersects the detection plane of the detector 13. The distance f can be represented as mathematical expression (3) and the intersection position ($x_c$, $y_c$) can be represented as mathematical expression (4).

[Expression 3]

-continued $$f = w[C - T] \quad (3)$$

[Expression 4]

$$\begin{bmatrix} x_c \\ y_c \end{bmatrix} = \begin{bmatrix} \frac{w-1}{2} \\ \frac{h-1}{2} \end{bmatrix} + \begin{bmatrix} \frac{1}{s_u} & 0 \\ 0 & \frac{1}{s_v} \end{bmatrix} \begin{bmatrix} u[C-T] \\ v[C-T] \end{bmatrix} \quad (4)$$

The second deriver 122b derives the re-projection error based on mathematical expression (5). Since the positions and directions of the detectors 13-1 and 13-2 in the three-dimensional space are known, as described above, parameters to be optimized are the three-dimensional position $T^j(\rightarrow)$ of the radiation source 12 and the three-dimensional positions $X^i(\rightarrow)$ of the markers MK.

[Expression 5]

$$\left(\hat{T}^1, \cdots \hat{T}^M, \hat{X}^1, \cdots \hat{X}^N\right) = \underset{T^1, \cdots T^M, X^1, \cdots X^N}{\mathrm{argmin}} \frac{1}{MN} \sum_{i=1}^{M} \sum_{j=1}^{N} [x^{ij} - \bar{x}^{ij}]^t [x^{ij} - \bar{x}^{ij}] \quad (5)$$

For example, the second deriver 122b may perform optimization of the two types of parameters of the three-dimensional position $T^j(\rightarrow)$ of the radiation source 12 and the three-dimensional positions $X^i(\rightarrow)$ of the markers MK using an optimization method called particle swarm optimization. Particle swarm optimization is an optimization method that imitates behaviors of a large group of insects and a method of searching for optimum positions while updating positions and speeds of particles during communication between particles by causing particles to have position and speed information of a search space. Although the position and direction of the detector 13 are assumed to be known in the present embodiment, when the three-dimensional position of the radiation source 12 is assumed to be known, the second deriver 122b may employ the center position $C^j(\rightarrow)$ of the detection plane of the detector 13 (the center position of the transparent image TI), the base vector $R^j(\rightarrow)$, and three-dimensional positions $X^i(\rightarrow)$ of the markers MK as the parameters to be optimized. In this manner, the position of each imaging device provided in the rotary gantry G can be estimated even when known parameters are any of the positions of the detectors 13 or the radiation sources 12. The known parameters may be any of the positions and direction of the detectors 13 and the positions of the radiation sources 12 or parameters corresponding to combinations thereof.

Next, the second deriver 122b causes the storage 130 to store the derived three-dimensional positions $T^j(\rightarrow)$ of the radiation sources 12 (12-1 and 12-2) as reference positions of the radiation sources 12 which will be referred to in the next and following processes (step S116). Accordingly, processing of this flowchart ends. The reference positions of the radiation sources 12 are, for example, parameters referred to during calibration performed in a second cycle shorter than the first cycle. The second cycle is, for example, a period of approximately one day or several days.

Figure 8:
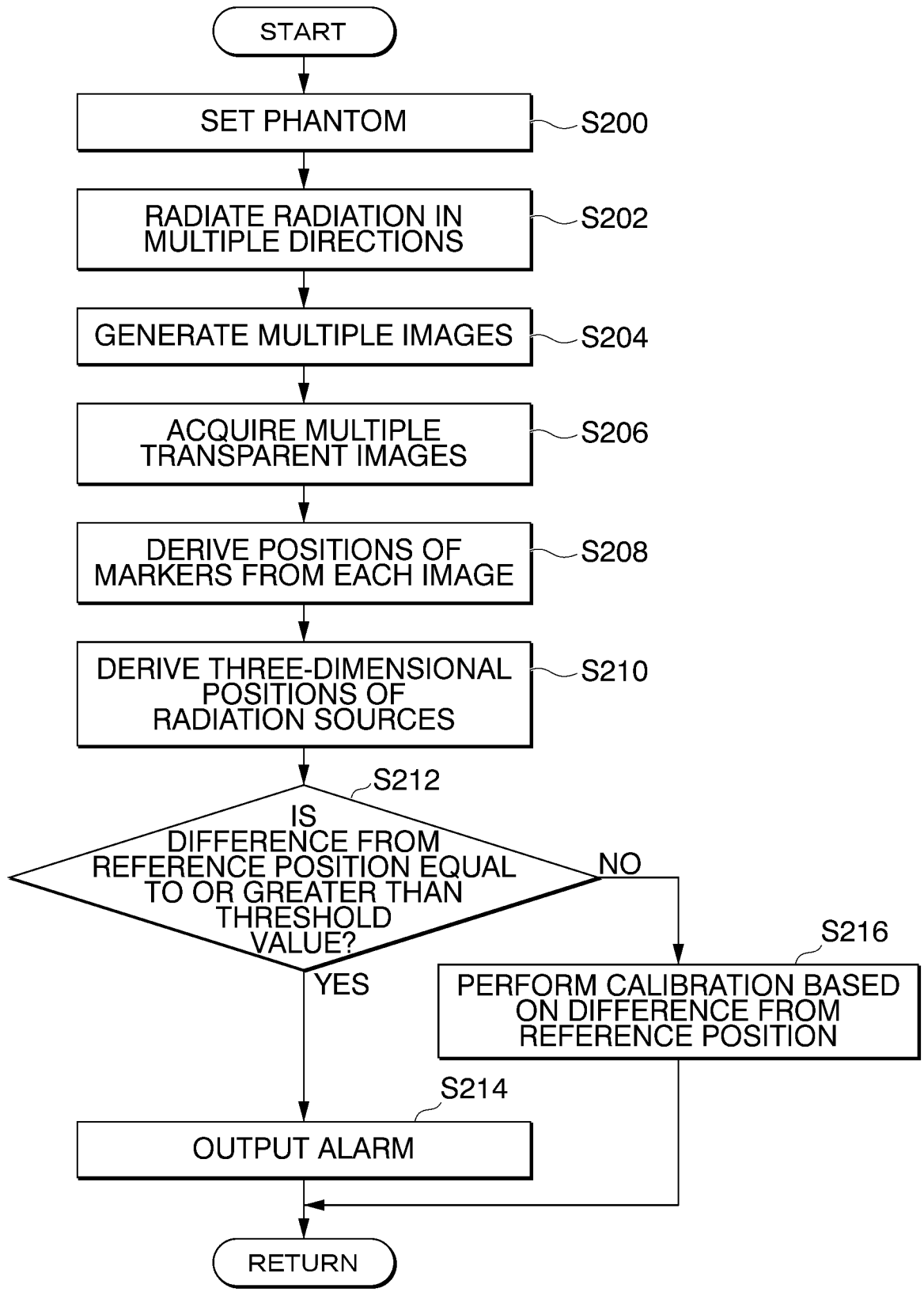
FIG. 8 is a flowchart showing another example of the calibration processing.

Hereinafter, calibration performed in the second cycle will be described using a flowchart. FIG. 8 is a flowchart showing another example of the calibration processing. Processing of this flowchart is repeatedly performed in the second cycle, for example.

First, a medical professional or the like sets a phantom having four or more markers embedded therein inside the rotary gantry G such that the phantom is projected to a transparent image TI (step S200).

Next, the medical professional or the like inputs information about completion of setting of the phantom to the inputter 104. Upon reception of this information, the treatment apparatus controller 16 of the treatment apparatus 10 selects two radiation sources 12 from the plurality of radiation sources 12 and causes the two selected radiation sources 12 to radiate X-rays in a plurality of different directions (step S202).

Next, the detectors 13-1 and 13-2 generate transparent images TI of the phantom PH in a plurality of directions (step S204).

Next, the first acquirer 112 acquires a plurality of transparent images TI from the detectors 13-1 and 13-2 through the communicator 102 (step S206).

Next, the first deriver 122a derives positions of markers MK with respect to each of the plurality of transparent images TI acquired by the first acquirer 112 (step S208).

Next, the second deriver 122b derives three-dimensional positions of the radiation sources 12-1 and 12-2 which are unknown parameters based on the positions of the markers MK derived from the transparent images TI and the position information acquired by the second acquirer 114 (step S210).

Next, the calibrator 122c derives differences between the three-dimensional positions of the radiation sources 12-1 and 12-2 derived by the second deriver 122b and the reference positions of the radiation sources 12-1 and 12-2 stored in the storage 130 and determines whether the differences are equal to or greater than a threshold value (step S212).

When known parameters are the three-dimensional positions of the radiation sources 12-1 and 12-2, the three-dimensional positions of the detectors 13-1 and 13-2 derived in calibration in the first cycle are stored as reference positions and three-dimensional directions thereof are stored as reference directions in the storage 130. In this case, the second deriver 122b derives the three-dimensional positions and the three-dimensional directions of the detectors 13-1 and 13-2 which are unknown parameters as processing of S210. Accordingly, when the known parameters are the three-dimensional positions of the radiation sources 12-1 and 12-2, the calibrator 122c may derive differences between the three-dimensional positions of the detectors 13-1 and 13-2 derived by the second deriver 122b and the reference positions and differences between the three-dimensional directions of the detectors 13-1 and 13-2 derived by the second deriver 122b and the reference directions and determine whether each difference is equal to or greater than a threshold value.

The information output controller 120 outputs an alarm representing that maintenance is necessary to the medical professional or the like using the treatment apparatus 10 when the calibrator 122c determines that the differences are equal to or greater than the threshold value (step S214).

Figures 9, 10:
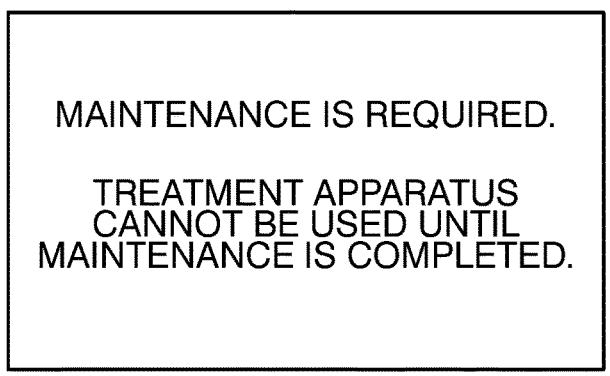
FIG. 9 is a diagram showing an example of a screen displayed on a display.
FIG. 10 is a diagram showing an example of treatment plan data.

For example, the information output controller 120 causes the display 106 to display an image as shown in FIG. 9 as an exemplary example of an alarm. FIG. 9 is a diagram showing an example of a screen displayed on the display 106. As in the illustrated example, text or an image representing that maintenance is required may be displayed on the screen of the display 106.

The information output controller 120 may output a mail or push notification for requesting maintenance to the terminal apparatus 20 as an alarm through the communicator 102.

Meanwhile, the calibrator 122c performs calibration based on differences from the reference positions (or reference directions) upon determining that the differences are less than the threshold value (step S216).

For example, the calibrator 122c may use the differences from the reference positions (or reference directions) as a correction amount and perform geometric transformation, such as an affine transformation, of a DRR as calibration based on the correction amount. The calibrator 122c may perform an affine transformation of transparent images TI as calibration instead of or in addition to using the differences from the reference positions (or reference directions) as a correction amount and performing an affine transformation of a DRR based on the correction amount.

The calibrator 122c may use the differences from the reference positions (or reference directions) as a correction amount and correct parameters referred to when a DRR is generated based on the correction amount as calibration. The parameters include, for example, the position and direction of each imaging device provided in the rotary gantry G. More specifically, the aforementioned parameters include the positions and/or directions of the detectors 13-1 and 13-2 and the positions of the radiation sources 12.

When the treatment apparatus 10 includes an adjustment mechanism which automatically controls the positions of the radiation sources 12 and the detectors 13, the calibrator 122c may adjust the position and direction of each imaging device by controlling the adjustment mechanism. According to such calibration, a DDR with high accuracy can be generated.

Although the treatment apparatus 10 is a treatment apparatus employing the rotary gantry G in the above description, the present invention is not limited thereto. For example, the treatment apparatus 10 may be a treatment apparatus in which the positions of imaging devices such as the radiation sources 12 are fixed (fixed port type).

When there are statistics in which a re-projection error is small in a certain direction and large in a certain direction, the calibration processor 122 may perform calibration based on transparent images TI captured in a direction in which the re-projection error decreases.

According to the above-described first embodiment, it is possible to calibrate the imaging system of the treatment apparatus 10 with high accuracy even when three-dimensional positions of markers MK are not known or known three-dimensional positions of markers MK include an error by including the rotary gantry G including one or more radiation sources 12 which radiate radiation to a certain object in a plurality of different directions and a plurality of detectors 13 which detect the radiation radiated from the radiation sources 12 at different positions as imaging devices, the first acquirer 112 which acquires a plurality of transparent images TI based on radiation detected by the plurality of detectors 13, the second acquirer 114 which acquires position information of the radiation sources 12 or the detectors 13, the first deriver 122a which derives positions of markers MK in a phantom PH in each of the plurality of transparent images TI acquired by the first acquirer 112, the second deriver 122b which derives a three-dimensional position and the like of an imaging device for which position information has not been acquired based on the positions of the markers MK in the transparent images TI derived by the first deriver 122a and three-dimensional positions of the radiation sources 12 or three-dimensional positions and three-dimensional directions of the detectors 13 represented by the position information acquired by the second acquirer 114, and the calibrator 122c which performs calibration of the rotary gantry G based on a derivation result of the second deriver 122b. As a result, it is possible to determine the position of a test object with high accuracy and track a target with high accuracy during treatment.

In general, radiation with sufficient power needs to be correctly radiated to an affected part of a patient when radiation treatment is performed. Accordingly, the patient is positioned by comparing an image of the patient acquired when treatment is planned with an image of the patient captured when radiation is radiated, and with respect to an affected part moving due to respiration, the affected part is tracked through transparent images TI according to X-rays after positioning and radiation is radiated thereto. To position this patient and perform affected part tracking with high accuracy, the imaging system needs to have been calibrated. However, when three-dimensional positions of markers MK are unknown or known three-dimensional positions of markers MK include an error, there are cases in which the position of a test object cannot be determined with high accuracy or a target cannot be tracked with high accuracy.

In particular, when calibration is performed, a larger error than assumed is easily generated in known three-dimensional positions of markers MK because the phantom PH is set in a frame and imaged. For example, in the case of a treatment apparatus in which the rotary gantry G is not employed and the positions of imaging devices such as the radiation sources 12 and the like are fixed, it is conceivable that a frame in a rectangular parallelepiped shape is installed on the floor of a treatment room and the phantom PH is disposed on the frame. However, in the case of the treatment apparatus 10 employing the rotary gantry G as in the present embodiment, there are cases in which it is difficult to install a frame in a rectangular parallelepiped shape on the floor because the radiation sources 12 is laid on the floor of the treatment room. Accordingly, there are cases in which an L-shaped frame is installed at a position separated from positions at which the radiation sources 12 are laid, for example. Here, the L-shaped frame is installed on the floor in such a manner that one side of the L-shaped edges is grounded to the floor and the other side is hanging in the air. For example, the phantom PH is disposed on the edge on the side hanging in the air between the edges of the L-shaped frame. In the L-shaped frame, minute distortion such as downward warping of the edge on the side hanging in the air in the vertical direction may be generated due to moment of force. In such a case, an error in the position of the phantom PH easily becomes larger than an originally assumed error. On the other hand, even when the phantom PH is disposed on the bed 11 or the like without preparing a frame, a dimensional error and the like of the arm 11a connected from the floor to the bed are integrated and thus an error in the position of the phantom PH easily becomes larger than the originally assumed error. In this manner, an error is easily generated in the position of the phantom PH when the phantom PH is set in the treatment room. When an error is generated in the position of the phantom PH, the three-dimensional position and three-dimensional directions of the detectors 13 and the three-dimensional positions of the radiation sources 12 also include errors and thus calibration accuracy easily decreases.

In contrast, in the present embodiment, the three-dimensional position of any imaging device provided in the rotary gantry G is measured in advance using a laser tracker and thus an unknown three-dimensional position of an imaging device can be derived even when positions of markers MK are not known. As a result, it is possible to calibrate the imaging system of the treatment apparatus 10 with high accuracy, determine the position of a test object with high accuracy and track a target with high accuracy.

The above-described medical image processing apparatus 100 may be realized by a general apparatus including a processor such as a CPU or a GPU and a storage device such as a ROM, a RAM, an HDD or a flash memory, the storage device storing a program for causing the processor to serve as the rotary gantry G including one or more radiation sources 12 which radiate radiation to a certain object in a plurality of different directions and a plurality of detectors 13 which detect the radiation radiated from the radiation sources 12 at different positions as imaging devices, the first acquirer 112 which acquires a plurality of transparent images TI based on radiation detected by the plurality of detectors 13, the second acquirer 114 which acquires position information of the radiation sources 12 or the detectors 13, the first deriver 122a which derives positions of markers MK in a phantom PH in each of the plurality of transparent images TI acquired by the first acquirer 112, the second deriver 122b which derives a three-dimensional position and the like of an imaging device for which position information has not been acquired based on the positions of the markers MK in the transparent images T1 derived by the first deriver 122a and three-dimensional positions of the radiation sources 12 or three-dimensional positions and three-dimensional directions of the detectors 13 represented by the position information acquired by the second acquirer 114, and the calibrator 122c which performs calibration of the rotary gantry G based on a derivation result of the second deriver 122b.

Second Embodiment

Hereinafter, a second embodiment will be described. The second embodiment differs from the above-described first embodiment in that transparent images T1 that are position derivation targets during calibration are selected based on a treatment plan of a patient. Hereinafter, a description will focus on differences from the first embodiment and description of common points in the first and second embodiments will be omitted. In a description of the second embodiment, the same parts as those in the first embodiment are denoted by the same reference signs and described.

FIG. 10 is a diagram showing an example of the treatment plan data 134. For example, the treatment plan data 134 is information in which a treatment date and time is associated with a treatment plan such as a radiation angle θ of the treatment beam B radiated during treatment for each patient.

The first deriver 122a in the second embodiment selects a transparent image TI that is a target from which positions of markers MK will be derived from a plurality of transparent images TI acquired by the first acquirer 112 and derives the positions of the markers MK in the selected transparent image TI.

For example, when a timing at which calibration in the second cycle is performed is set to early morning of each day, the first deriver 122a selects a patient scheduled to receive treatment after calibration from a plurality of patients scheduled to receive treatment in a treatment plan. For example, when the treatment plan is the one illustrated in FIG. 10 and a timing at which calibration in the second cycle is performed is "early morning Jun. 1, 2020," the first deriver 122a selects patients A, B and C scheduled to receive treatment on that day. Then, the first deriver 122a selects transparent images TI that are targets from which positions of markers MK will be derived based on radiation angles θ of treatment beams B associated with the selected patients A, B and C.

Figure 11:
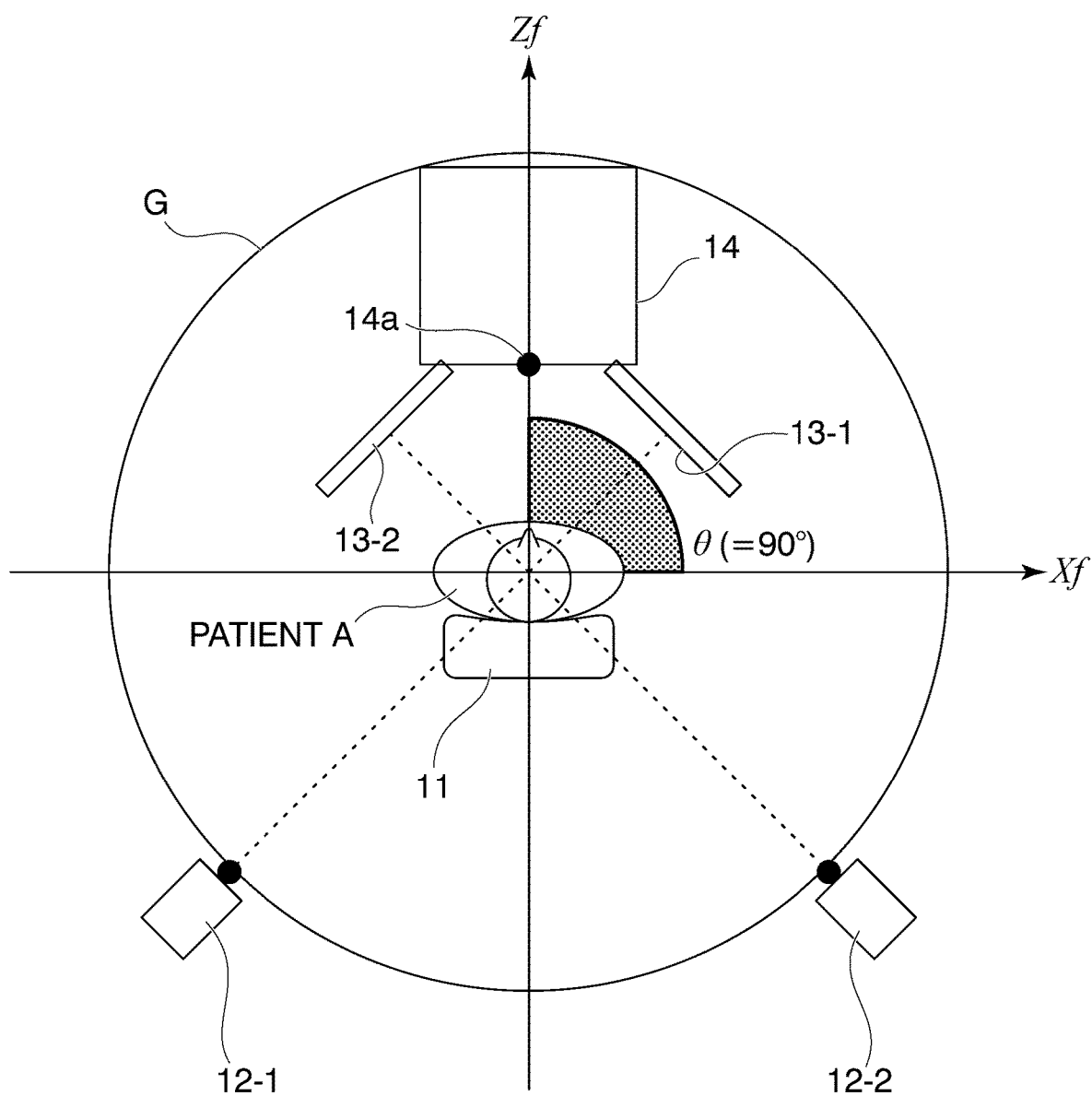
FIG. 11 is a diagram showing a transparent image selection method based on a treatment plan.
Figure 12:
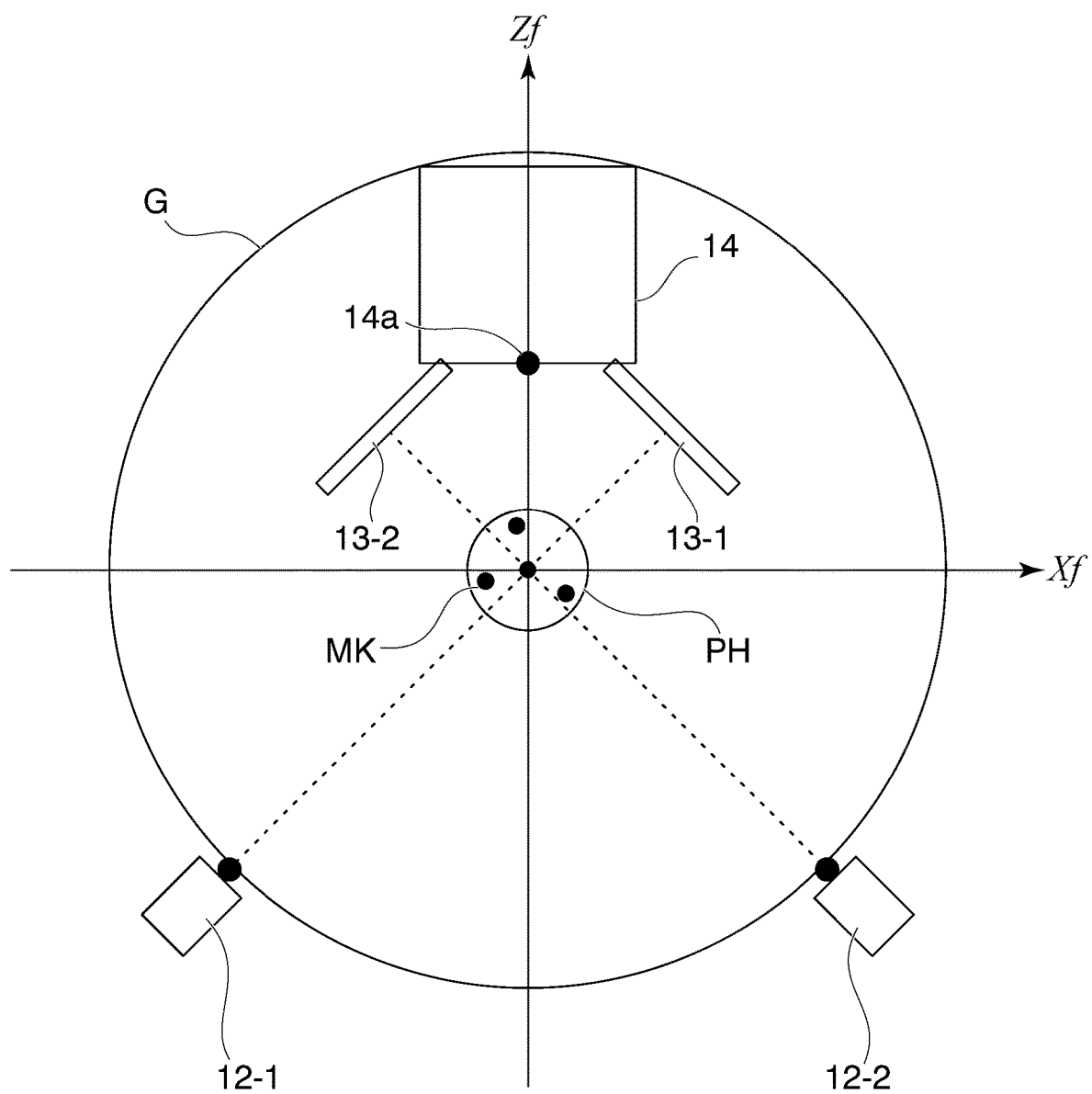
FIG. 12 is a diagram showing a transparent image selection method based on a treatment plan.

FIG. 11 and FIG. 12 are diagrams showing a method of selecting a transparent image TI based on a treatment plan. For example, when an angle between a horizontal direction $X_f$ that passes through the rotation axis center and a radiation direction of the treatment beam B of the radiating gate 14 is assumed to be a radiation angle θ of the treatment beam B in the angle around the rotation axis of the rotary gantry G, the first deriver 122a selects transparent images TT generated based on X-rays radiated from the radiation sources 12-1 and 12-2 when the rotary gantry G has been rotated at the angle θ. For example, in the case of a patient A, the first deriver 122a selects a transparent image TI capturing markers MK according to X-rays radiated from the radiation sources 12-1 and 12-2 when the phantom PH including the markers MK is disposed inside the rotary gantry G and the rotary gantry G has been rotated at an angle at which the treatment beam B is radiated to the patient A from right above, as shown in FIG. 12, because the radiation angle θ of the treatment beam B is 90°. Accordingly, it is possible to omit calibration with respect to radiation directions of the treatment beam B which are not used for treatment on that day.

According to the above-described second embodiment, it is possible to reduce a time required for calibration compared to a case in which 360° omni-directional calibration is performed because transparent images T1 that are position derivation targets during calibration are selected based on a treatment plan of a patient.

According to at least one of the above-described embodiments, it is possible to calibrate the imaging system of the treatment apparatus 10 with high accuracy even when three-dimensional positions of markers MK are not known or known three-dimensional positions of markers MK include an error by including the rotary gantry G which includes, as imaging devices, one or more radiation sources 12 which radiate radiation to a certain object in a plurality of different directions and a plurality of detectors 13 which detect the radiation radiated from the radiation sources 12 at different positions, the first acquirer 112 which acquires a plurality of transparent images TI based on radiation detected by the plurality of detectors 13, the second acquirer 114 which acquires position information of the radiation sources 12 or the detectors 13, the first deriver 122a which derives positions of markers MK in a phantom PH in each of the plurality of transparent images TI acquired by the first acquirer 112, the second deriver 122b which derives a three-dimensional position and the like of an imaging device for which position information has not been acquired based on the positions of the markers MK on the transparent images TI derived by the first deriver 122a and three-dimensional positions of the radiation sources 12 or three-dimensional positions and three-dimensional directions of the detectors 13 represented by the position information acquired by the second acquirer 114, and the calibrator 122c which performs calibration of the rotary gantry G based on a derivation result of the second deriver 122b. As a result, it is possible to determine the position of a test object with high accuracy and track a target with high accuracy during treatment.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A treatment system comprising:
an imaging system comprising, as imaging devices, one or more radiation sources which are configured to radiate radiation to a certain object in a plurality of different directions, and a plurality of detectors which are configured to detect the radiation radiated from the radiation sources at different positions;
a first acquirer which is configured to acquire a plurality of images based on the radiation detected by the plurality of detectors;
a second acquirer which is configured to acquire position information representing at least one of a position and a direction of a first imaging device included in the imaging system in a three-dimensional space in which the imaging system is disposed;
a first deriver which is configured to derive a position of the object in each of the plurality of images acquired by the first acquirer;
a second deriver which is configured to derive at least one of a position and a direction of a second imaging device included in the imaging system in the three-dimensional space based on the position of the object in the images derived by the first deriver and the position or the direction of the first imaging device represented by the position information acquired by the second acquirer; and
a calibrator which is configured to perform calibration of the imaging system based on a derivation result of the second deriver.

2. The treatment system according to claim 1, wherein the imaging system is installed in a rotary gantry, and
the treatment system further comprises a radiation controller which is configured to cause the rotary gantry to rotate and cause the radiation sources to radiate radiation while changing positions of the radiation sources with respect to the object.

3. The treatment system according to claim 1, wherein the object includes four or more markers,
wherein at least one of the four or more markers is present on a second plane different from a first plane on which the other three or more markers are present in the three-dimensional space in the object.

4. The treatment system according to claim 1, wherein the second deriver is further configured to derive the position of the object in the three-dimensional space based on the position of the object in the images derived by the first deriver and the position or the direction of the first imaging device represented by the position information acquired by the second acquirer.

5. The treatment system according to claim 1, further comprising a particle beam source which is configured to radiate a particle beam different from radiation radiated from the radiation sources to a test object,
wherein the first deriver is configured to select an image that is a target from which the position of the object will be derived from the plurality of images acquired by the first acquirer based on a treatment plan associated with a radiation direction of the particle beam radiated by the particle beam source for each test object, and derive the position of the object in the selected image.

6. The treatment system according to claim 5, wherein the first driver is configured to select the test object to which the particle beam is scheduled to be radiated after calibration of the imaging system from a plurality of test objects to which the particle beam is scheduled to be radiated in the treatment plan, and
wherein an image based on the radiation radiated in the same direction as a radiation direction of the particle beam associated with the selected test object is selected from the plurality of images acquired by the first acquirer as an image that is a target from which the position of the object will be derived.

7. The treatment system according to claim 1, further comprising an image processor which is configured to generate a virtual two-dimensional image when viewed at a certain view based on three-dimensional images obtained by arranging images based on the radiation detected by the detectors in the radiation direction of the radiation,
wherein the calibrator is configured to perform a geometric transformation of the two-dimensional image generated by the image processor as the calibration based on the derivation result of the second deriver.

8. The treatment system according to claim 1, wherein the calibrator is configured to perform a geometric transformation of the images acquired by the first acquirer as the calibration based on the derivation result of the second deriver.

9. The treatment system according to claim 1, further comprising an image processor which is configured to generate a virtual two-dimensional image when viewed at a certain view based on three-dimensional images obtained by arranging images based on the radiation detected by the detectors in the radiation direction of the radiation,
wherein the calibrator is configured to perform correction of parameters referred to when the image processor generates the two-dimensional image as the calibration based on the derivation result of the second deriver.

10. The treatment system according to claim 1, further comprising:
an outputter which outputs information; and
an output controller which is configured to control the outputter to output information for requesting adjustment of the position or the direction of the imaging system to a terminal apparatus of a user who performs maintenance of the imaging system when a first difference between the position of the second imaging device in the three-dimensional space derived by the second deriver and a reference position or a second difference between the direction of the second imaging device in the three-dimensional space derived by the second deriver and a reference direction is equal to or greater than a threshold value.

11. The treatment system according to claim 10, wherein the second deriver is configured to repeat derivation of at least one of the position and the direction of the second imaging device in the three-dimensional space in each of a first cycle and a second cycle shorter than the first cycle,
the reference position is a position of the second imaging device in the three-dimensional space derived by the second deriver in the first cycle,
the reference direction is a direction of the second imaging device in the three-dimensional space derived by the second deriver in the first cycle,
the first difference is a difference between the position of the second imaging device in the three-dimensional space derived by the second deriver in the second cycle and the reference position, and the second difference is a difference between the direction of the second imaging device in the three-dimensional space derived by the second deriver in the second cycle and the reference direction.

12. A calibration method by a computer which is configured to control an imaging system comprising, as imaging devices, one or more radiation sources which are configured to radiate radiation to a certain object in a plurality of different directions, and a plurality of detectors which are configured to detect the radiation radiated from the radiation sources at different positions, the calibration method comprising:

acquiring a plurality of images based on the radiation detected by the plurality of detectors;

acquiring position information representing at least one of a position and a direction of a first imaging device included in the imaging system in a three-dimensional space in which the imaging system is disposed;

deriving a position of the object in each of the plurality of acquired images;

deriving at least one of a position and a direction of a second imaging device included in the imaging system in the three-dimensional space based on the position of the object in the derived images and the position or the direction of the first imaging device represented by the acquired position information; and performing calibration of the imaging system based on the derived position or direction of the second imaging device in the three-dimensional space.

13. A non-transitory computer-readable storage medium storing a program for causing a computer which controls an imaging system comprising, as imaging devices, one or more radiation sources which are configured to radiate radiation to a certain object in a plurality of different directions, and a plurality of detectors which are configured to detect the radiation radiated from the radiation sources at different positions to execute:

processing of acquiring a plurality of images based on the radiation detected by the plurality of detectors;

processing of acquiring position information representing at least one of a position and a direction of a first imaging device included in the imaging system in a three-dimensional space in which the imaging system is disposed;

processing of deriving a position of the object in each of the plurality of acquired images;

processing of deriving at least one of a position and a direction of a second imaging device included in the imaging system in the three-dimensional space based on the position of the object in the derived images and the position or the direction of the first imaging device represented by the acquired position information; and processing of performing calibration of the imaging system based on the derived position or direction of the second imaging device in the three-dimensional space.

* * * * *